US006625818B2

(12) United States Patent
Putnam

(10) Patent No.: US 6,625,818 B2
(45) Date of Patent: Sep. 30, 2003

(54) CAP WITH BIAXIAL SWEATBAND AND OTHER ADJUSTABLE HEADGEAR

(75) Inventor: John Putnam, Vernon, CA (US)

(73) Assignee: Putnam Sourcing Group, Inc., Vernon, CA (US)

( * ) Notice: Subject to any disclaimer, the term of this patent is extended or adjusted under 35 U.S.C. 154(b) by 0 days.

(21) Appl. No.: 10/045,727

(22) Filed: Jan. 11, 2002

(65) Prior Publication Data

US 2003/0131395 A1 Jul. 17, 2003

(51) Int. Cl.[7] .................................................. A42C 5/00
(52) U.S. Cl. ........................................................ 2/181
(58) Field of Search ...................... 2/181, 181.2, 181.4, 2/209.13, 195.1

(56) References Cited

U.S. PATENT DOCUMENTS

| | | | | |
|---|---|---|---|---|
| 3,280,406 A | * | 10/1966 | Immel | 2/181 |
| 5,966,742 A | | 10/1999 | Cunliffe | 2/195.3 |
| 6,131,202 A | | 10/2000 | Yan | 2/195.3 |
| 6,347,410 B1 | * | 2/2002 | Lee | 2/181 |
| 6,499,144 B1 | * | 12/2002 | Yan | 2/181.2 |

* cited by examiner

Primary Examiner—John J. Calvert
Assistant Examiner—Katherine Moran
(74) Attorney, Agent, or Firm—Cislo & Thomas LLP

(57) ABSTRACT

A headwear item such as a cap, having a mutiaxially stretchable band is provided. The band comprises multiple layers of uniaxially or multiaxially stretchable material connected with elastic stitching for making the band multi-axially stretchable. Such biaxially stretchable band may utilize any fabric that is uniaxially or biaxially stretchable for the layers of the band, allowing for a wide variety of fabrics to be utilized. Additionally, the elastic stitching between the layers of the band provide for varying space between the layers, making the band lighter, and providing comfort and breathability to the wearer.

13 Claims, 4 Drawing Sheets

CAP WITH BIAXIAL SWEATBAND AND OTHER ADJUSTABLE HEADGEAR

BACKGROUND OF THE INVENTION

1. Field of the Invention

This invention relates to a headwear item which is adjustable to a user's head size.

2. Description of the Related Art

In the past, a various methods have been employed to construct a hat or other head worn items that are adjustable to fit a user's head size. For example, baseball caps have been constructed with an adjustable strap and closure mechanism, such as plastic snaps, VELCRO and metal buckles, usually located opposite the visor of the cap. Headwear constructed with such adjustable closure systems requires the user to adjust the headwear to fit his head. As such, an incorrect adjustment can be uncomfortable if too tight or may fall off the user's head if too loose. Additionally, the closing mechanism may come undone inadvertently.

Various alternative arrangements utilizing a stretchable band for making a headwear item adjustable to fit a user's head have also been developed. (see U.S. Pat. No. 5,615,415 issued to Beckerman; U.S. Pat. No. 5,715,540 issued to Cho; U.S. Pat. No. 5,966,742 issued to Cunliff; and U.S. Pat. No. 6,199,213 B1 issued to Whang).

SUMMARY OF THE INVENTION

The present invention provides for a headwear item such as a cap, having a mutiaxially stretchable band comprising several layers of material which is at least uniaxially stretchable, connected with elastic stitching, making the band multiaxially stretchable. Such multiaxially stretchable band may utilize any fabric that is uniaxially or biaxially stretchable for the layers, allowing for a wide variety of fabrics to be utilized. Additionally, the elastic stitching between the layers of the band provide for varying space between the layers, making the band more comfortable and providing increased breathability.

OBJECTS OF THE INVENTION

It is an object of the present invention to provide headwear items which are adjustable to a user's head size.

It is a further object of the present invention to provide headwear items which are comfortable to wear.

It is a further object of the present invention to provide a headwear item utilizing a multiaxially stretchable band which provides for breathability to the user's head.

These and other objects and advantages of the present invention will be apparent from a review of the following specification and accompanying drawings.

BRIEF DESCRIPTION OF THE DRAWINGS

FIG. 3b is a bottom plan view of the cap of FIG. 3a.

DESCRIPTION OF THE PREFERRED EMBODIMENTS

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Figure 1:
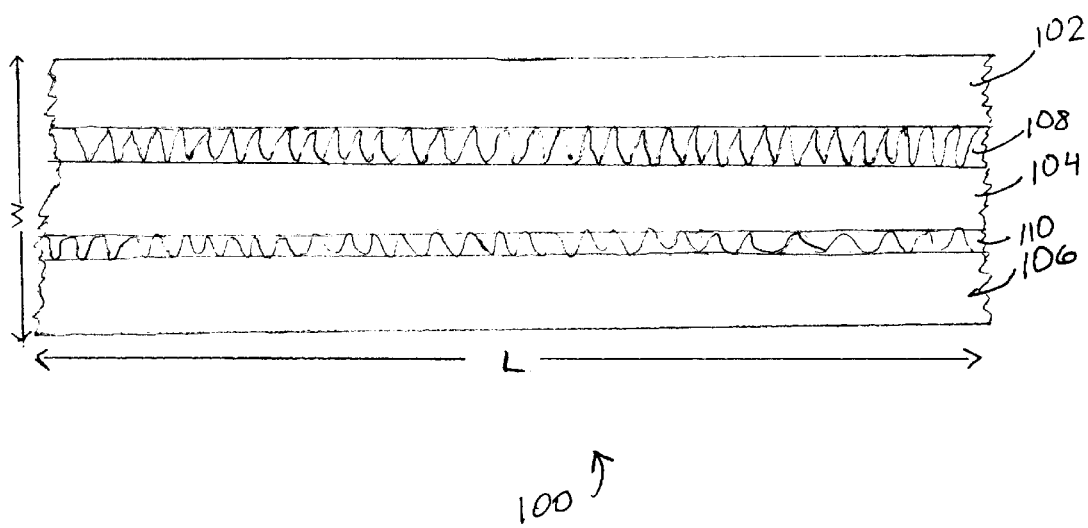
FIG. 1 is an elevation view of a segment of a band according to an embodiment of the present invention.

FIG. 1 illustrates a multiaxially stretchable multilayer band 100 according to a preferred embodiment of the present invention. Only a segment of the band is shown in the illustration, however, the band may be of any length "L" depending on the application. For example, the band may form a loop that can be worn around the head of a user, or may be incorporated into a headwear item either fully encircling the head or forming a partial segment covering only a part of the rim of the headwear item. While certain types of headwear items are illustrated, it is to be understood that a multiaxially stretchable multilayer band according to the present invention, may be incorporated in a variety of headwear items including caps, hats, visor hats, helmets and the like.

The band has multiple layers of stretchable fabric 102, 104, 106 with elastic stitching 108, 110 between the layers securing the layers to each other in a parallel alignment. Although three layers are illustrated in the figure, any number of layers may be used, with two layers being the minimum.

The layers 102, 104, 106 may be of any fabric that is uniaxially or multiaxially stretchable, as long as the layers are stretchable at least along the length "L" of the band. Sweat absorbent fabrics such as cotton, or may be especially desirable for headgear designed to be worn during exercise. The layers 102, 104, and 106 are preferably of the same fabric each, but may also be of varying fabric, types, or varying patterns and colors. Additionally, while the layers 102, 104, and 106 are illustrated as being of approximately equal widths, they may also be of varying widths.

The stitching 108, 110 between the fabrics 102, 104, 106 allows for the band 100 to stretch along the width "W" of the band, while maintaining the bands stretchability along the length L. The stitching also provides spacing between the layers giving the band breathability. Most commercially available elastic threads are suitable for the stitching. A highly porous and elastic fabric may also be sewn between the layers to achieve breathability and widthwise stretchability of the band. As with the fabric layers, the stitching 108 and 110 may be of a similar pattern or may vary. Additionally, different layers of stitching may provide varying degrees of spacing between the fabric layers.

Figure 2:
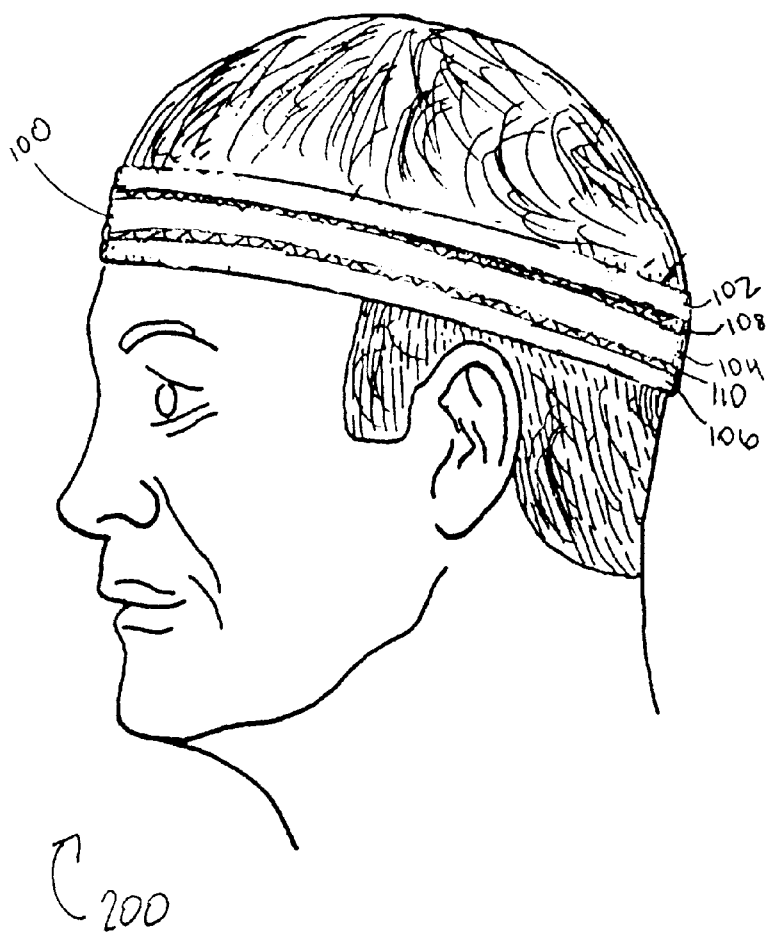
FIG. 2 is an elevation view of the band of FIG. 1 worn on a user's head.

FIG. 2 illustrates the band 100 worn around the head of a user 200. In this embodiment, the band 100 forms an enclosed loop around the head. The multi layered band 100 may also be used to form a segment of the loop to be worn around the user's head while the rest of the loop may be formed from any other material which may be stretchable or unstretchable. Depending on the stretchability of the fabrics used, a band having an unstretched circumference of approximately 57–59 cm will stretch when worn on the head to accommodate a range of different head sizes.

Figure 3A:
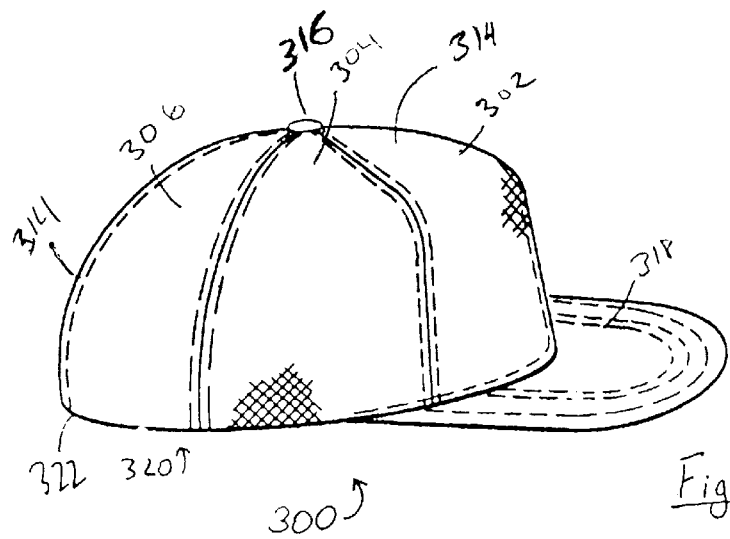
FIG. 3a is a perspective view of a cap incorporating the band of FIG. 1.
Figure 3B:
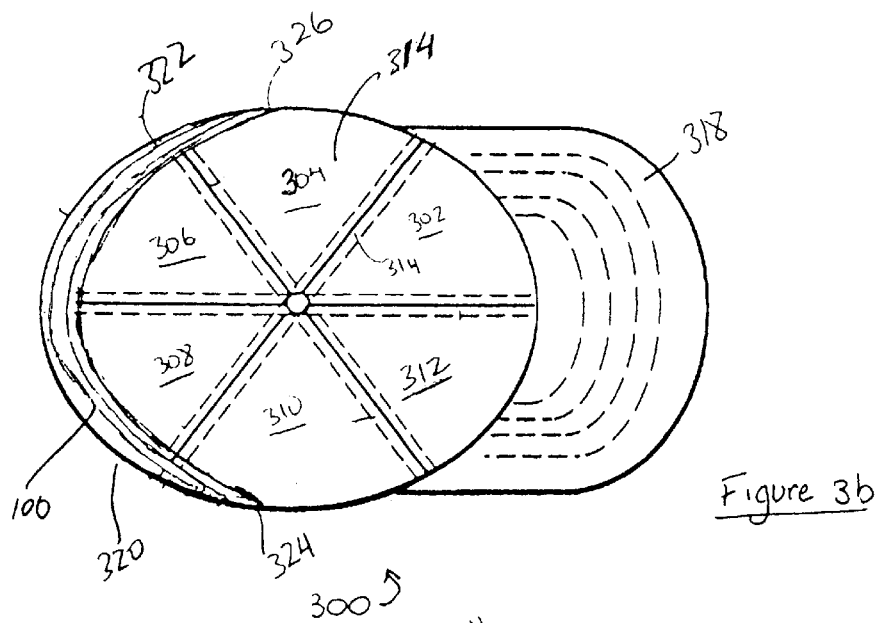
Figure 3C:
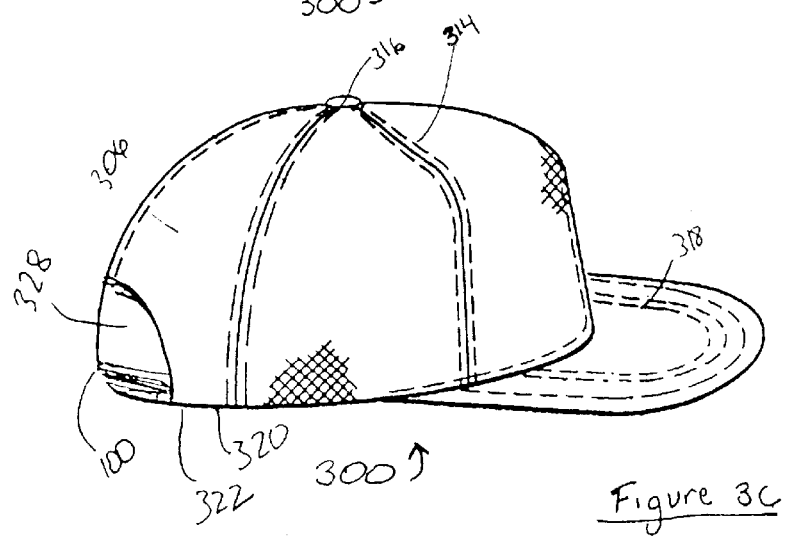
FIG. 3c is a perspective view of the cap of FIG. 3a having a cut out portion, and incorporating the band of FIG. 1.

FIGS. 3a–c illustrate a cap 300 incorporating the band 100 for making the cap adjustable to fit a range of head sizes. The cap 300 is a typical baseball cap formed from a plurality of generally triangular panels or gores 302, 304, 306, 308, 310, 312, which are secured together (e.g. by sewing) along their adjacent side edges forming a crown 314 with their apices meeting at the top of the crown 316. Additionally, the cap 300 has a visor 318.

The band 100 is preferably secured along the inner circumference 320 of the crown 314, with a lengthwise edge of the band secured along the rim 322 of the crown. The band may be secured by stitching, lamination, or other suitable methods. The band 100 may extend along a segment of the circumference as shown in FIG. 3b or along the entire circumference.

According to one embodiment, a band 100 covering a segment of the circumference is located opposite the visor 318. The band may be secured by stitching the band to the crown at the outer edges of the band 324 and at locations where the gores intersect. The cap may utilize gores made from a fabric that is stretchable in the circumferential direction for at least the portion of the cap incorporating the band 100 (gores 304, 306, 308 and 310 for the cap of FIG. 3b) such that the cap will stretch with the band. Alternatively, the unstretched band length may be made smaller than the arc length of the rim portion to which the band is secured, such that the band has room to stretch without having to stretch the cap.

According to another embodiment, the cap 300 may have a cut out portion 328 extending upwardly from the rim, and interrupting the continuity of the rim, opposite the visor 318, with the band 100 being interiorly attached and covering the lower section of the cut out portion 328 to complete the continuity of the rim 322, as illustrated in FIG. 3c.

Figure 4:
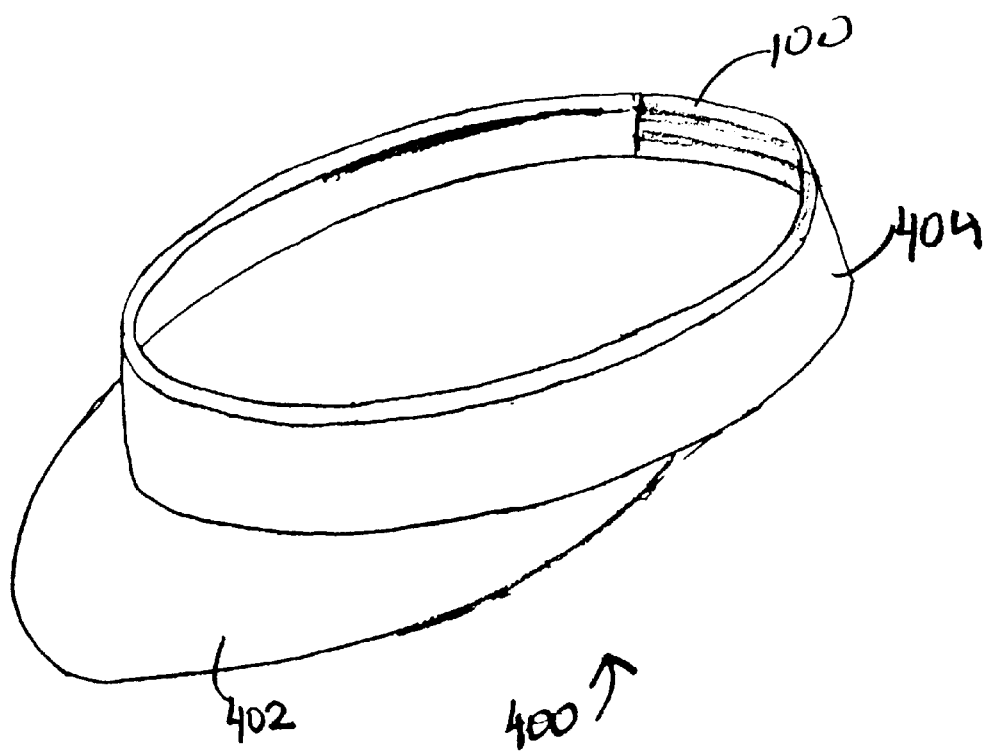
FIG. 4 is a perspective view of a visor cap incorporating a band according to an embodiment of the present invention.

FIG. 4 illustrates a visor hat 400 incorporating the band 100. The hat 400 has a visor 402 and an open portion 404 encircling the head and having a rim. As shown in the figure, the band may be secured to the inside circumference of the portion 404 forming a partial segment of the portion 404 preferably at a side opposite the visor 402, making the visor hat stretchable to fit a user's head. Other embodiments of a visor hat incorporating a band such that it fully encircles the head are also contemplated.

While the present invention has been described with regards to particular embodiments, it is recognized that additional variations of the present invention may be devised without departing from the inventive concept.

What is claimed is:

1. A band comprising:
   a plurality of fabric layers each having a length and being stretchable at least in a direction along said length;
   said fabric layers each having adjacent lengthwise side edges and being arranged relative to each other in a parallel alignment; and
   a separate elastic element securing each pair of adjacent lengthwise side edges;
   wherein said band is stretchable both along its length and in a direction orthogonal to its length, and
   wherein said elastic element provides varying spacing between the layers.

2. The band of claim 1 wherein said elastic element comprises elastic thread stitching for securing the layers to each other.

3. The band of claim 1 wherein said band forms a closed loop to be worn around the head of a user.

4. The article of claim 1 wherein said fabric layers include at least one layer which has a sweat absorbent quality.

5. A headwear article comprising:
   a band comprising
      a plurality of fabric layers each having a length and being stretchable at least in a direction along said length;
      said fabric layers each having adjacent lengthwise side edges and being arranged relative to each other in a parallel alignment; and
      a separate elastic element securing each pair of adjacent lengthwise side edges;
      wherein said band is stretchable both along its length and in a direction orthogonal to its length, and
   wherein said elastic element provides varying spacing between the layers; and
   a cap comprising a plurality of gores integrated into a crown and having apices meeting at the top of the crown, said gores forming a rim having a circumference opposite said top;
   wherein said band is integrated with said crown, in a parallel alignment with said circumference, making the cap adjustable to a user's head size.

6. The article of claim 5 wherein said band is secured at an interior side of said crown, with a lengthwise side edge of the band being secured along said rim.

7. The article of claim 5 wherein said band forms a closed loop over the entire circumference formed by said gores.

8. The article of claim 5 wherein said band is aligned over a partial segment of said circumference said crown.

9. The article of claim 5 wherein at least one of said gores is stretchable along the circumferential direction of said crown.

10. The article of claim 5 wherein the unstretched length of the band is smaller than the arc length of the rim portion to which the band is secured, such that the band has room to stretch without stretching the cap.

11. The article of claim 5 wherein said cap further includes a visor secured at one side of said crown.

12. The article of claim 5 wherein said cap includes a cut out portion extending upwardly from said rim, said cut out portion interrupting the continuity of said rim, wherein said band extends around said cut out portion, completing said rim.

13. A headwear article comprising:
   a band comprising
      a plurality of fabric layers each having a length and being stretchable at least in a direction along said length;
      said fabric layers each having adjacent lengthwise side edges and being arranged relative to each other in a parallel alignment; and
      a separate elastic element securing each pair of adjacent lengthwise side edges;
      wherein said band is stretchable both along its length and in a direction orthogonal to its length, and
   wherein said elastic element provides varying spacing between the layers
   a cap comprising a plurality of gores integrated into a crown and having apices meeting at the top of the crown, said gores forming a rim having a circumference opposite said top;
   wherein said band is integrated with said crown, in a parallel alignment with said circumference, making the cap adjustable to a user's head size; and
   a visor hat, said visor hat comprising:

a visor, and an open portion for encircling the head of a user, said open portion having a rim, with said visor being coupled to said open portion, wherein said band is integrated with said open portion making the hat adjustable to said user's head size.

* * * * *